(12) United States Patent
Jahnke et al.

(10) Patent No.: US 9,061,131 B2
(45) Date of Patent: Jun. 23, 2015

(54) DISPOSABLE ACOUSTIC COUPLING MEDIUM CONTAINER

(75) Inventors: Russell C. Jahnke, Ann Arbor, MI (US);
James A. Bertolina, Portage, MI (US);
William W. Roberts, Saline, MI (US);
Charles A. Cain, Ann Arbor, MI (US);
Dejan Teofilovic, Ann Arbor, MI (US);
Thomas W. Davison, Naples, FL (US)

(73) Assignees: HISTOSONICS, INC., Ann Arbor, MI (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 330 days.

(21) Appl. No.: 12/858,242

(22) Filed: Aug. 17, 2010

(65) Prior Publication Data

US 2011/0040190 A1    Feb. 17, 2011

Related U.S. Application Data

(60) Provisional application No. 61/234,559, filed on Aug. 17, 2009.

(51) Int. Cl.
*A61B 8/00* (2006.01)
*A61N 7/00* (2006.01)
*A61B 8/12* (2006.01)
(Continued)

(52) U.S. Cl.
CPC ... *A61N 7/00* (2013.01); *A61B 8/12* (2013.01); *A61B 17/2251* (2013.01); *A61B 17/2256* (2013.01); *A61B 2017/00274* (2013.01); *A61B 2017/2253* (2013.01); *A61B 2018/00547* (2013.01); *A61B 2019/5276* (2013.01);
(Continued)

(58) Field of Classification Search
USPC .......................................... 600/439; 601/2-3
See application file for complete search history.

(56) References Cited

U.S. PATENT DOCUMENTS

| 3,243,497 A | 3/1966 | Kendall et al. |
| 3,679,021 A | 7/1972 | Goldberg et al. |

(Continued)

FOREIGN PATENT DOCUMENTS

| DE | 3220751 | 12/1983 |
| DE | 3544628 A1 | 6/1987 |

(Continued)

OTHER PUBLICATIONS

Hall et al.; Imaging feedback of tissue liquefaction (histotripsy) in ultrasound surgery; IEEE Ultrasonic Symposium, Sep. 18-21, 2005, pp. 1732-1734.

(Continued)

*Primary Examiner* — Long V Le
*Assistant Examiner* — Ellsworth Weatherby
(74) *Attorney, Agent, or Firm* — Shay Glenn LLP

(57) ABSTRACT

A medical imaging and therapy device is provided that may include any of a number of features. One feature of the device is that it can acoustically couple an ultrasound therapy transducer to a patient. In some embodiments, the medical imaging and therapy device is configured to conform to the anatomy of a patient's perineal area to acoustically couple an ultrasound therapy transducer to the patient for treatment of BPH. The medical imaging and therapy device can be used in therapeutic applications such as Histotripsy, Lithotripsy, and HIFU, for example. Methods associated with use of the medical imaging and therapy device are also covered.

15 Claims, 7 Drawing Sheets

(51) Int. Cl.
*A61B 17/225* (2006.01)
*A61B 17/00* (2006.01)
*A61B 18/00* (2006.01)
*A61B 19/00* (2006.01)

(52) U.S. Cl.
CPC . *A61N2007/0039* (2013.01); *A61N 2007/0043* (2013.01); *A61B 8/445* (2013.01)

(56) References Cited

U.S. PATENT DOCUMENTS

| | | | |
|---|---|---|---|
| 4,024,501 A | 5/1977 | Herring et al. |
| 4,051,394 A | 9/1977 | Tieden |
| 4,117,446 A | 9/1978 | Alais |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,453,408 A | 6/1984 | Clayman |
| 4,483,345 A | 11/1984 | Miwa |
| 4,549,533 A | 10/1985 | Cain et al. |
| 4,550,606 A | 11/1985 | Drost |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,938,217 A | 7/1990 | Lele |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,209,221 A | 5/1993 | Riedlinger |
| 5,215,680 A | 6/1993 | D'Arrigo |
| 5,219,401 A | 6/1993 | Cathignol et al. |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,469,852 A | 11/1995 | Nakamura et al. |
| 5,474,071 A | 12/1995 | Chapelon et al. |
| 5,474,531 A | 12/1995 | Carter |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,694,936 A | 12/1997 | Fujimoto et al. |
| 5,695,460 A | 12/1997 | Siegel et al. |
| 5,717,657 A | 2/1998 | Ruffa |
| 5,724,972 A | 3/1998 | Petrofsky |
| 5,743,863 A | 4/1998 | Chapelon |
| 5,753,929 A | 5/1998 | Bliss |
| 5,759,162 A * | 6/1998 | Oppelt et al. ............ 601/2 |
| 5,766,138 A * | 6/1998 | Rattner .................... 601/4 |
| 5,769,790 A | 6/1998 | Watkins et al. |
| 5,797,848 A | 8/1998 | Marian et al. |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,932,807 A | 8/1999 | Mallart |
| 5,947,904 A | 9/1999 | Hossack et al. |
| 6,001,069 A | 12/1999 | Tachibana et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A * | 10/2000 | Whitmore et al. ........... 600/459 |
| 6,128,958 A | 10/2000 | Cain |
| 6,143,018 A | 11/2000 | Beuthan et al. |
| 6,176,842 B1 | 1/2001 | Tachibana et al. |
| 6,308,585 B1 | 10/2001 | Nilsson et al. |
| 6,308,710 B1 * | 10/2001 | Silva ........................ 128/849 |
| 6,309,355 B1 | 10/2001 | Cain et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 * | 9/2003 | Weng et al. ................. 601/3 |

(56) References Cited

U.S. PATENT DOCUMENTS

| | | | |
|---|---|---|---|
| 6,645,162 B2 | 11/2003 | Friedman et al. | |
| 6,648,839 B2 | 11/2003 | Manna et al. | |
| 6,666,833 B1 | 12/2003 | Friedman et al. | |
| 6,685,640 B1 | 2/2004 | Fry et al. | |
| 6,685,657 B2 | 2/2004 | Jones | |
| 6,705,994 B2 | 3/2004 | Vortman et al. | |
| 6,719,449 B1 | 4/2004 | Laugharn, Jr. et al. | |
| 6,719,694 B2 | 4/2004 | Weng et al. | |
| 6,735,461 B2 | 5/2004 | Vitek et al. | |
| 6,736,814 B2 | 5/2004 | Manna et al. | |
| 6,750,463 B1 | 6/2004 | Riley | |
| 6,770,031 B2 | 8/2004 | Hynynen et al. | |
| 6,775,438 B1 | 8/2004 | Gaedke et al. | |
| 6,788,977 B2 | 9/2004 | Fenn et al. | |
| 6,790,180 B2 | 9/2004 | Vitek | |
| 6,820,160 B1 | 11/2004 | Allman | |
| 6,852,082 B2 | 2/2005 | Strickberger et al. | |
| 6,869,439 B2 | 3/2005 | White et al. | |
| 6,890,332 B2 | 5/2005 | Truckai et al. | |
| 6,929,609 B2 | 8/2005 | Asafusa | |
| 7,004,282 B2 | 2/2006 | Manna et al. | |
| 7,059,168 B2 | 6/2006 | Hibi et al. | |
| 7,128,711 B2 | 10/2006 | Medan et al. | |
| 7,128,719 B2* | 10/2006 | Rosenberg | 601/2 |
| 7,175,596 B2 | 2/2007 | Vitek et al. | |
| 7,196,313 B2 | 3/2007 | Quinones | |
| 7,223,239 B2 | 5/2007 | Schulze et al. | |
| 7,258,674 B2 | 8/2007 | Cribbs et al. | |
| 7,273,458 B2 | 9/2007 | Prausnitz et al. | |
| 7,273,459 B2 | 9/2007 | Desilets et al. | |
| 7,300,414 B1 | 11/2007 | Holland et al. | |
| 7,311,679 B2 | 12/2007 | Desilets et al. | |
| 7,331,951 B2 | 2/2008 | Eshel et al. | |
| 7,341,569 B2 | 3/2008 | Soltani et al. | |
| 7,347,855 B2 | 3/2008 | Eshel et al. | |
| 7,358,226 B2 | 4/2008 | Dayton et al. | |
| 7,359,640 B2 | 4/2008 | Onde et al. | |
| 7,367,948 B2 | 5/2008 | O'Donnell et al. | |
| 7,374,551 B2 | 5/2008 | Liang et al. | |
| 7,377,900 B2 | 5/2008 | Vitek et al. | |
| 7,442,168 B2 | 10/2008 | Novak et al. | |
| 7,462,488 B2 | 12/2008 | Madsen et al. | |
| 7,559,905 B2* | 7/2009 | Kagosaki et al. | 601/3 |
| 7,656,638 B2 | 2/2010 | Laakso et al. | |
| 2001/0039420 A1 | 11/2001 | Burbank et al. | |
| 2001/0041163 A1 | 11/2001 | Sugita et al. | |
| 2002/0045890 A1 | 4/2002 | Celliers et al. | |
| 2002/0078964 A1* | 6/2002 | Kovac et al. | 128/850 |
| 2002/0099356 A1 | 7/2002 | Unger et al. | |
| 2003/0092981 A1 | 5/2003 | Eppstein | |
| 2003/0112922 A1 | 6/2003 | Burdette et al. | |
| 2003/0149352 A1 | 8/2003 | Liang et al. | |
| 2003/0157025 A1 | 8/2003 | Unger et al. | |
| 2003/0181833 A1 | 9/2003 | Faragalla et al. | |
| 2003/0199857 A1 | 10/2003 | Eizenhofer | |
| 2003/0221561 A1 | 12/2003 | Milo | |
| 2004/0127815 A1 | 7/2004 | Marchitto et al. | |
| 2004/0138563 A1 | 7/2004 | Moehring et al. | |
| 2004/0236248 A1 | 11/2004 | Svedman | |
| 2004/0243021 A1 | 12/2004 | Murphy et al. | |
| 2005/0038339 A1 | 2/2005 | Chauhan et al. | |
| 2005/0038361 A1 | 2/2005 | Zhong et al. | |
| 2005/0152561 A1 | 7/2005 | Spencer | |
| 2005/0154314 A1 | 7/2005 | Quistgaard | |
| 2005/0283098 A1 | 12/2005 | Conston et al. | |
| 2006/0060991 A1 | 3/2006 | Holsteyns et al. | |
| 2006/0074303 A1 | 4/2006 | Chornenky et al. | |
| 2006/0206028 A1 | 9/2006 | Lee et al. | |
| 2006/0241466 A1 | 10/2006 | Ottoboni et al. | |
| 2006/0241523 A1 | 10/2006 | Sinelnikov et al. | |
| 2006/0264760 A1 | 11/2006 | Liu et al. | |
| 2006/0293630 A1* | 12/2006 | Manna et al. | 604/327 |
| 2007/0010805 A1 | 1/2007 | Fedewa et al. | |
| 2007/0016039 A1 | 1/2007 | Vortman et al. | |
| 2007/0065420 A1 | 3/2007 | Johnson | |
| 2007/0083120 A1* | 4/2007 | Cain et al. | 600/439 |
| 2007/0161902 A1 | 7/2007 | Dan | |
| 2007/0167764 A1 | 7/2007 | Hynynen | |
| 2007/0205785 A1 | 9/2007 | Nilsson | |
| 2007/0219448 A1 | 9/2007 | Seip et al. | |
| 2008/0013593 A1 | 1/2008 | Kawabata | |
| 2008/0055003 A1 | 3/2008 | Unnikrishnan et al. | |
| 2008/0082026 A1 | 4/2008 | Schmidt et al. | |
| 2008/0126665 A1 | 5/2008 | Burr et al. | |
| 2008/0214964 A1 | 9/2008 | Chapelon et al. | |
| 2008/0262345 A1 | 10/2008 | Fichtinger et al. | |
| 2008/0262486 A1 | 10/2008 | Zvuloni et al. | |
| 2008/0312561 A1 | 12/2008 | Chauhan | |
| 2008/0319356 A1 | 12/2008 | Cain et al. | |
| 2009/0030339 A1 | 1/2009 | Cheng et al. | |
| 2009/0112098 A1 | 4/2009 | Vaezy et al. | |
| 2009/0177085 A1 | 7/2009 | Maxwell et al. | |
| 2009/0198094 A1 | 8/2009 | Fenster et al. | |
| 2009/0211587 A1* | 8/2009 | Lawrentschuk | 128/850 |
| 2009/0227874 A1 | 9/2009 | Suri et al. | |
| 2010/0011845 A1 | 1/2010 | Laugharn et al. | |
| 2010/0069797 A1 | 3/2010 | Cain et al. | |
| 2010/0125225 A1* | 5/2010 | Gelbart et al. | 601/3 |
| 2010/0163694 A1 | 7/2010 | Fadler et al. | |
| 2010/0261994 A1 | 10/2010 | Davalos et al. | |
| 2010/0286519 A1 | 11/2010 | Lee et al. | |
| 2010/0317971 A1 | 12/2010 | Fan et al. | |
| 2011/0112400 A1 | 5/2011 | Emery et al. | |
| 2011/0118602 A1 | 5/2011 | Weng et al. | |
| 2011/0172529 A1 | 7/2011 | Gertner | |
| 2011/0178444 A1 | 7/2011 | Slayton et al. | |
| 2011/0251528 A1 | 10/2011 | Canney et al. | |
| 2012/0010541 A1 | 1/2012 | Cain et al. | |
| 2012/0029353 A1 | 2/2012 | Slayton et al. | |
| 2012/0130288 A1 | 5/2012 | Holland et al. | |
| 2012/0189998 A1 | 7/2012 | Kruecker et al. | |
| 2013/0053691 A1 | 2/2013 | Kawabata et al. | |
| 2013/0090579 A1 | 4/2013 | Cain et al. | |
| 2013/0102932 A1 | 4/2013 | Cain et al. | |
| 2013/0190623 A1 | 7/2013 | Bertolina et al. | |
| 2013/0303906 A1 | 11/2013 | Cain et al. | |
| 2014/0073995 A1 | 3/2014 | Teofilovic et al. | |
| 2014/0100459 A1 | 4/2014 | Xu et al. | |

FOREIGN PATENT DOCUMENTS

| | | |
|---|---|---|
| DE | 3817094 A1 | 11/1989 |
| EP | 0017382 A1 | 10/1980 |
| EP | 0320303 A2 | 6/1989 |
| EP | 0332871 A2 | 9/1989 |
| EP | 0384831 A2 | 8/1990 |
| EP | 0755653 A1 | 1/1997 |
| EP | 1504713 A1 | 2/2005 |
| GB | 2099982 A | 12/1982 |
| JP | 60-80779 A | 5/1985 |
| JP | 61-196718 A | 8/1986 |
| JP | HEI 2-215451 | 8/1990 |
| JP | HEI 6-197907 A | 7/1994 |
| JP | HEI 7-504339 A | 5/1995 |
| JP | 08-84740 A | 4/1996 |
| JP | 06-304178 A | 5/1996 |
| JP | 08-131454 A | 5/1996 |
| JP | HEI 10-512447 | 12/1998 |
| JP | 2003-510159 A | 3/2003 |
| JP | 2004-505660 A | 2/2004 |
| JP | 2007520307 | 7/2007 |
| JP | 2010029650 A | 2/2010 |
| JP | 2004-512502 A | 4/2014 |
| WO | WO94/06355 A1 | 3/1994 |
| WO | WO 02/32506 A1 | 4/2002 |
| WO | WO 2008/051484 A2 | 5/2008 |
| WO | WO 2011/092683 A1 | 8/2011 |

OTHER PUBLICATIONS

Cain, Charles A.; Histrotripsy: controlled mechanical sub-division of soft tissues by high intensity pulsed ultrasound (conference presentation); International Symposium on Therapeutic Ultrasound; pp. T005; 2005.

(56) References Cited

OTHER PUBLICATIONS

Hall et al.; Ultrasound imaging feedback of tissue liquefaction in ultrasound surgery; Ultrasonics Symposium; IEEE; vol. 3; pp. 1732-1734; Sep. 18-21, 2005.
Parsons et al.; Pulsed cavitational ultrasound therapy for controlled tissue homogenization; Ultrasound in Med. & Biol.; vol. 32; pp. 115-129; 2006.
Roberts et al.; Pulsed cavitational ultrasound: a noninvasive technology for controlled tissue ablation (histotripsy) in the rabbit kidney; Journal of Urology; vol. 175; pp. 734-738; 2006.
Xu et al.; A new strategy to enhance cavitational tissue erosion by using a high intensity initiating sequence; IEEE Trans Ultrasonics Ferroelectrics and Freq Control; vol. 53; pp. 1412-1424; 2006.
Xu et al.; Controlled ultrasound tissue erosion: the role of dynamic interaction between insonation and microbubble activity; Journal of the Acoustical Society of America; vol. 117; pp. 424-435; 2005.
Xu et al.; Controlled ultrasound tissue erosion; IEEE Transaction on Ultrasonics, Ferroelectrics, and Frequency Control; vol. 51; pp. 726-736; 2004.
Xu et al.; Effects of acoustic parameters on bubble cloud dynamics in ultrasound tissue erosion (histotripsy); Journal of the Acoustical Society of America; vol. 122; pp. 229-236; 2007.
Xu et al.; High Speed Imaging of Bubble Clouds Generated in Pulsed Ultrasound Cavitational Therapy'Histotripsy; IEEE Trans Ultrason Ferroelectr Freq Control; ; vol. 54; No. 10; pp. 2091R2101; Oct. 2007.
Xu et al.; Investigation of intensity threshold for ultrasound tissue erosion; Ultrasound in Med. & Biol.; vol. 31; pp. 1673-1682; 2005.
Xu et al.; Optical and acoustic monitoring of bubble cloud dynamics at a tissue-fluid interface in ultrasound tissue erosion; Journal of the Acoustical Society of America; vol. 121; pp. 2421-2430; 2007.
Hall et al.; U.S. Appl. No. 12/868,768 entitled "Micromanipulator Control Arm for Therapeutic and Imaging Ultrasound Transducers," filed Aug. 26, 2010.
Cain et al.; U.S. Appl. No. 12/868,775 entitled "Devices and Methods for Using Controlled Bubble Cloud Cavitation in Fractionating Urinary Stones," filed Aug. 26, 2010.
Cain et al.; U.S. Appl. No. 12/887,705 entitled "Gel phantoms for testing cavitational ultrasound (histotripsy) transducers," filed Sep. 22, 2010.
Appel et al.; Stereoscopic highspeed recording of bubble filaments; Ultrasonics Sonochemistry; vol. 11(1); pp. 39-42; Jan. 2004.
Atchley et al.; Thresholds for cavitation produced in water by pulsed ultrasound; Ultrasonics.; vol. 26(5); pp. 280-285; Sep. 1988.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and No. Of transient cavities in the field of an electromagnetic lithotripter; Physics in Medicine and Biology; vol. 43 (10); pp. 3113-3128; Oct. 1998.
Lauterborn et al.; Cavitation bubble dynamics studied by high speed photography and holography: part one; Ultrasonics; vol. 23; pp. 260-268; Nov. 1985.
Miller et al.; A review of in vitro bioeffects of inertial ultrasonic cavitation from a mechanistic perspective; Ultrasound in Medicine and Biology; vol. 22; pp. 1131-1154; (year of publication is sufficiently earlier than the effective U.S. filed and any foreign priority date) 1996.
Ohl et al.; Bubble dynamics, shock waves and sonoluminescence; Phil. Trans. R. Soc. Lond. A; vol. 357; pp. 269-294; (year of publication is sufficiently earlier than the effective U.S. filed and any foreign priority date) 1999.

Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Roy et al.; A precise technique for the measurement of acoustic cavitation thresholds and some preliminary results; Journal of the Acoustical Society of America; vol. 78(5); pp. 1799-805; Nov. 1985.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sokolov et al.; Use of a dual-pulse lithotripter to generate a localized and intensified cavitation field; Journal of the Acoustical Society of America; vol. 110(3); pp. 1685-1695; Sep. 2001.
Teofilovic, Dejan; U.S. Appl. No. 13/446,783 entitled "Systems and Methods for Obtaining Large Creepage Isolation on Printed Boards," filed Apr. 13, 2012.
Cain, Charles A.; U.S. Appl. No. 13/570,708 entitled "Lesion Generation Through Bone Using Histotripsy Therapy Without Aberration Correction," filed Aug. 9, 2012.
Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clement et al.; A hemisphere array for non-invasive ultrasound brain therapy and surgery; Physics in Medicine and Biology, vol. 45, p. 3707-3719, Dec. 2000.
Desilets et al.; The Design of Efficient Broad-Band Piezoelectric Transducers; Sonics and Ultrasonics, IEEE Transactions on, vol. 25, pp. 115-125, May 1978.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System for Transcutaneous Ultrasound Surgery; AIP Conference Proceedings, Boston, MA; vol. 829, pp. 445-449, Oct. 27-29, 2005.
Hall et al.; Histotripsy of the prostate: dose effects in a chronic canine model; Urology; 74(4); pp. 932-937; Oct. 2009 (author manuscript).
Hartmann; Ultrasonic properties of poly(4-methyl pentene-1), Journal of Applied Physics, vol. 51, pp. 310-314, Jan. 1980.
Kim et al.; Dependence of particle volume fraction on sound velocity and attenuation of EPDM composites; Ultrasonics, vol. 46, pp. 177-183, Feb. 2007.
Krimholtz et al.; New equivalent circuits for elementary piezoelectric transducers; Electronics Letters, vol. 6, pp. 398-399, Jun. 1970.
Lake et al.; Histotripsy: minimally invasive technology for prostatic tissue ablation in an in vivo canine model; Urology; 72(3); pp. 682-686; Sep. 2008.
Lensing et al.; Deep-vein thrombosis; The Lancet, vol. 353, pp. 479-485, Feb. 6, 1999.
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al; Effect of Radial Displacement of Lens on Response of Focused Ultrasonic Transducer; Japanese Journal of Applied Physics, vol. 46, p. 3077-3085; May 15, 2007.
Maréchal et al; Lens-focused transducer modeling using an extended KLM model; Ultrasonics, vol. 46, pp. 155-167, May 2007.

(56) References Cited

OTHER PUBLICATIONS

Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Sato et al.; Experimental Investigation of Phased Array Using Tapered Matching Layers. 2002 IEEE Ultrasound Symposium. vol. 2; pp. 1235-1238, Oct. 2002.
Simonin et al.; Characterization of heterogeneous structure in a polymer object manufactured by stereolithography with low-frequency microechography; Journal of Materials Chemistry; vol. 6, pp. 1595-1599, Sep. 1996.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.
Van Kervel et al.; A calculation scheme for the optimum design of ultrasonic transducers; Ultrasonics, vol. 21, pp. 134-140, May 1983.
Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009 (author manuscript).
Yan et al.; A review of rapid prototyping technologies and systems; Computer-Aided Design, vol. 28, pp. 307-318, Apr. 1996.
Hall et al.; U.S. Appl. No. 13/874,083 entitled "Ultrasound Transducer Manufacturing Using Rapid-Prototyping Method," filed Apr. 30, 2013.
Avago Technologies; ACNV2601 High Insulation Voltage 10 MBd Digital Opotcoupler. Avago Technologies Data Sheet; pp. 1-11; Jul. 29, 2010.
Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Emelianov et al.; Triplex ultrasound: Elasticity imaging to age deep venous thrombosis; Ultrasound Med Biol; 28(6); pp. 757-767; Jun. 2002.
Hynynen et al.; Tissue thermometry during ultrasound exposure; European Urology; 23(Suppl 1); pp. 12-16; 1993 (year of pub. sufficiently earlier than effective US filed and any foreign priority date)
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Konofagou; Quo vadis elasticity imaging?; Ultrasonics; 42(1-9); pp. 331-336; Apr. 2004.
Kruse et al.; Tissue characterization using magnetic resonance elastography: Preliminary results; Phys. Med. Biol; 45(6); pp. 1579-1590; Jun. 2000.
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Nightingale et al.; Analysis of contrast in images generated with transient acoustic radiation force; Ultrasound Med Biol; 32(1); pp. 61-72; Jan. 2006.
Okada et al.; A case of hepatocellular carcinoma treated by MR-guided focused ultrasound ablation with respiratory gating; Magn Reson Med Sci; 5(3); pp. 167-171; Oct. 2006.
Rowland et al.; MRI study of hepatic tumours following high intensity focused ultrasound surgery; British Journal of Radiology; 70; pp. 144-153; Feb. 1997.
Sapareto et al.; Thermal dose determination in cancer therapy; Int J Radiat Oncol Biol Phys; 10(6); pp. 787-800; Apr. 1984.
Souchon et al.; Visualisation of HIFU lesions using elastography of the human prostate in vivo: Preliminary results; Ultrasound Med. Biol; 29(7); pp. 1007-1015; Jul. 2003.
Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).
Zheng et al.; An acoustic backscatter-based method for localization of lesions induced by high-intensity focused ultrasound; Ultrasound Med Biol; 36(4); pp. 610-622; Apr. 2010.
Bjoerk et al.; Cool/MOS CP—How to make most beneficial use of the generation of super junction technology devices. Infineon Technologies AG. Feb. 2007 [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf?folderId=db3a304412b407950112b408e8c90004&fileId=db3a304412b407950112b40ac9a40688>pp. 1, 4, 14.
Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011[retrieved on Jan. 28, 2014] from the internet: (http://web.archive.org/web/20110720091822/http://www.histotripsy.umich.edu/index.html>. entiredocument).
Avtech; AVR-8 Data sheet; May 23, 2004; 3 pages; retrieved from the internet (http//www.avtechpulse.com).

* cited by examiner

DISPOSABLE ACOUSTIC COUPLING MEDIUM CONTAINER

CROSS REFERENCE TO RELATED APPLICATIONS

This application claims the benefit under 35 U.S.C. 119 of U.S. Provisional Patent Application No. 61/234,559, filed Aug. 17, 2009, titled "Disposable Acoustic Coupling Medium Container". This application is herein incorporated by reference in its entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

The present invention generally relates to acoustically coupling ultrasound devices to a patient. More specifically, the present invention relates to acoustically coupling ultrasound therapy devices to a patient for treatment of tissue.

BACKGROUND OF THE INVENTION

Histotripsy and Lithotripsy are non-invasive tissue ablation modalities that focus pulsed ultrasound from outside the body to a target tissue inside the body. Histotripsy mechanically damages tissue through cavitation of microbubbles, and Lithotripsy is typically used to fragment urinary stones with acoustic shockwaves.

Histotripsy is the mechanical disruption via acoustic cavitation of a target tissue volume or tissue embedded inclusion as part of a surgical or other therapeutic procedure. Histotripsy works best when a whole set of acoustic and transducer scan parameters controlling the spatial extent of periodic cavitation events are within a rather narrow range. Small changes in any of the parameters can result in discontinuation of the ongoing process.

Histotripsy requires high peak intensity acoustic pulses which in turn require large surface area focused transducers. These transducers are often very similar to the transducers used for Lithotripsy and often operate in the same frequency range. The primary difference is in how the devices are driven electrically.

Histotripsy pulses consist of a (usually) small number of cycles of a sinusoidal driving voltage whereas Lithotripsy is (most usually) driven by a single high voltage pulse with the transducer responding at its natural frequencies. Even though the Lithotripsy pulse is only one cycle, its negative pressure phase length is equal to or greater than the entire length of the Histotripsy pulse, lasting tens of microseconds. This negative pressure phase allows generation and continual growth of the bubbles, resulting in bubbles of sizes up to 1 mm. The Lithotripsy pulses use the mechanical stress produced by a shockwave and these 1 mm bubbles to cause tissue damage.

In comparison, each negative and positive cycle of a Histotripsy pulse grows and collapses the bubbles, and the next cycle repeats the same process. The maximal sizes of bubbles reach approximately tens to hundreds of microns. These micron size bubbles interact with a tissue surface to mechanically damage tissue.

In addition, Histotripsy delivers hundreds to thousands of pulses per second, i.e., 100-1 kHz pulse repetition frequency. Lithotripsy only works well within a narrow range of pulse repetition frequency (usually 0.5-1 Hz). Studies show that the efficacy and efficiency of lithotripsy decreases significantly when the pulse repetition frequency is increased to 10-100 Hz. The reduced efficiency is likely due to the increased number of mm size bubbles blocking the shock waves and other energy from reaching the stone.

Histotripsy transducers have a focal point positioned a distance from the transducer where the cavitational bubble clouds are formed. In order to non-invasively treat tissue inside a patient, the transducers must be positioned away from the patient's skin so as to locate the cavitational focal point on the target tissue. Thus, when the transducer is positioned away from the patient's skin, the pulsed ultrasound of a Histotripsy ultrasound transducer must be carried through an aqueous coupling medium that is in intimate contact with the ultrasound transducer and the skin surface.

One prior solution to acoustic coupling for therapeutic ultrasound includes a water bath disposed in a treatment table. During therapy, the patient lies with the body immersed in the water bath. This coupling solution is both cumbersome and expensive as it requires a specialized examination table and is not versatile or portable. Additionally, it requires a large volume of an acoustic coupling medium (typically degassed water) which is expensive and can be messy.

Thus, there is a need for an inexpensive, minimal, and versatile acoustic coupling device for use in ultrasonic therapy applications such as Histotripsy and Lithotripsy.

SUMMARY OF THE INVENTION

In one embodiment, a method of treating a prostate of a patient comprises imaging the prostate with an ultrasound probe, placing an acoustic medium container over a perineum of the patient, and applying ultrasonic therapy through the acoustic medium container to cause mechanical fractionation of a target portion of the prostate.

In one embodiment, the prostate can be imaged by inserting the ultrasound probe into the patient's rectum to image the prostate. In some embodiments, the ultrasound probe is inserted into a rectal sheath to provide a liquid seal barrier between the ultrasound probe and the patient's rectum.

In some embodiments, the method comprises at least partially filling the acoustic medium container with an acoustic coupling medium, such as degassed water. In some embodiments, the acoustic coupling medium directly contacts the patient's skin. In other embodiments, the acoustic coupling medium does not directly contact the patient's skin.

In other embodiments, the method further comprises securing the acoustic medium container to the patient with an adhesive. In other embodiments, the method comprises securing the acoustic medium container to the patient with a strap. The acoustic medium container can be secured to the patient to form a liquid seal between the container and the patient's skin.

The applying step can further comprise applying ultrasonic therapy with an ultrasonic therapy transducer coupled to the acoustic medium container. In some embodiments, the applying ultrasonic therapy step comprises applying histotripsy to treat the patient. In other embodiments, the applying ultrasonic therapy step comprises forming cavitation bubbles in the target portion of the prostate. In additional embodiments, the applying ultrasonic therapy step comprises applying acoustic pulses that operate at a frequency between approximately 50 KHz and 5 MHz, having a pulse intensity with a peak negative pressure of approximately 8-25 MPa, a peak positive pressure of more than 10 MPa, a pulse length shorter than 50 cycles, a duty cycle between approximately 0.1% and 5%, and a pulse repetition frequency of less than 5 KHz.

In additional embodiments, the applying ultrasonic therapy step comprises applying lithotripsy or HIFU to treat the patient.

In some embodiments, the method further comprises expelling a volume of the acoustic coupling medium into a remote reservoir from the acoustic medium container when the acoustic medium container is compressed, and infusing a volume of the acoustic coupling medium into the acoustic medium container from the remote reservoir when the acoustic medium container is expanded.

In another embodiment, an ultrasound therapy device is provided, comprising a frame configured to conform to and provide a liquid seal against a patient's skin, a reservoir portion configured to hold an acoustic coupling medium in direct contact with the patient's skin, and an, ultrasound transducer in acoustic communication with the acoustic coupling medium, wherein movement of the ultrasound transducer relative to the frame maintains acoustic communication between the ultrasound transducer and the acoustic coupling medium.

In some embodiments, the ultrasound therapy device further comprising a rectal imaging probe configured to image the patient's prostate. In one embodiment, the reservoir portion comprises a sheath configured to receive the rectal imaging probe.

In one embodiment, the frame is sized and shaped to conform to a male patient's anatomy surrounding the perineum.

In some embodiments of the ultrasound therapy device, the reservoir portion is pliable. In other embodiments, the reservoir portion is transparent. In another embodiment, the reservoir portion is open so as to expose the acoustic coupling medium to air.

In some embodiments, the ultrasound transducer is coupled to the reservoir portion and configured to direct ultrasonic therapy through the perineum to the patient's prostate.

In one embodiment, the ultrasound therapy device further comprises a sling configured to hold the patient's scrotum away from the perineum.

In one embodiment, the ultrasound transducer is submerged in the acoustic coupling medium.

In another embodiment, the reservoir portion is sealed to contain the acoustic coupling medium against the patient's skin.

In many embodiments, the acoustic coupling medium comprises a degassed water. In other embodiments, the acoustic coupling medium comprises an acoustic gel.

In some embodiments of the ultrasound therapy device, the frame is secured to the patient with an adhesive. In other embodiments, the frame is secured to the patient with a strap. In another embodiment, the frame comprises a wearable garment. The wearable garment can provide a liquid seal against the patient's skin near the patient's waist and near the patient's legs, for example. Alternatively, the wearable garment can provide a liquid seal against the patient's skin around the patient's perineum.

In some embodiments, the ultrasound therapy device further comprises a remote reservoir configured to receive the acoustic coupling medium from the reservoir portion when the reservoir portion is compressed and to deliver the acoustic coupling medium to the reservoir portion when the reservoir portion is expanded.

In some embodiments, the ultrasonic transducer is configured to deliver a histotripsy pulse to the patient's prostate. In another embodiment, the ultrasonic transducer is configured to form cavitation bubbles in the patient's prostate. In yet another embodiment, the ultrasonic transducer is configured to deliver acoustic pulses that operate at a frequency between approximately 50 KHz and 5 MHz, having a pulse intensity with a peak negative pressure of approximately 8-25 MPa, a peak positive pressure of more than 10 MPa, a pulse length shorter than 50 cycles, a duty cycle between approximately 0.1% and 5%, and a pulse repetition frequency of less than 5 KHz.

An ultrasound coupling container is also provided, comprising a frame configured to provide a liquid seal against a patient's skin, the frame including first and second portions sized and configured to conform to each side of the patient's groin, and a reservoir portion coupled to the frame and configured to allow positioning and movement of an ultrasound transducer over the patient's perineum and prostate.

In some embodiments, the ultrasound coupling container further comprises a rectal sheath coupled to the reservoir portion.

In another embodiment, the ultrasound coupling container further comprises a receptacle coupled to the reservoir portion, the receptacle configured to receive the ultrasound transducer.

In some embodiments, the reservoir portion is pliable.

In other embodiments, the frame comprises a third portion connecting the first and second portions, the third portion being configured to conform to the patient's skin below the rectum.

In some embodiments, the ultrasound coupling container further comprises a sling configured to hold the patient's scrotum away from the perineum.

In another embodiment, the frame is coupled to a wearable garment that is configured to be worn by the patient.

DETAILED DESCRIPTION OF THE INVENTION

In addition to imaging tissue, ultrasound technology is increasingly being used to treat and destroy tissue. In medical applications such as Histotripsy, where ultrasound pulses are used to form cavitational microbubbles in tissue to mechanically break down and destroy tissue, it is necessary to acoustically couple the ultrasound therapy transducer to the patient while allowing for movement of the therapy transducer in all directions. Particular challenges arise in the application of Histotripsy for the treatment of BPH and prostate cancer, where the male anatomy provides only a small acoustic window through the perineum to deliver ultrasound energy. The present invention describes several embodiments of an ultrasound coupling apparatus for acoustically coupling an ultrasound therapy transducer to a patient. In particular, the present invention provides for acoustic coupling of ultrasound therapy transducers, such as those used in Histotripsy, Lithotripsy, and HIFU, for the treatment of a variety of medical conditions including but not limited to BPH and prostate cancer.

Figure 1:
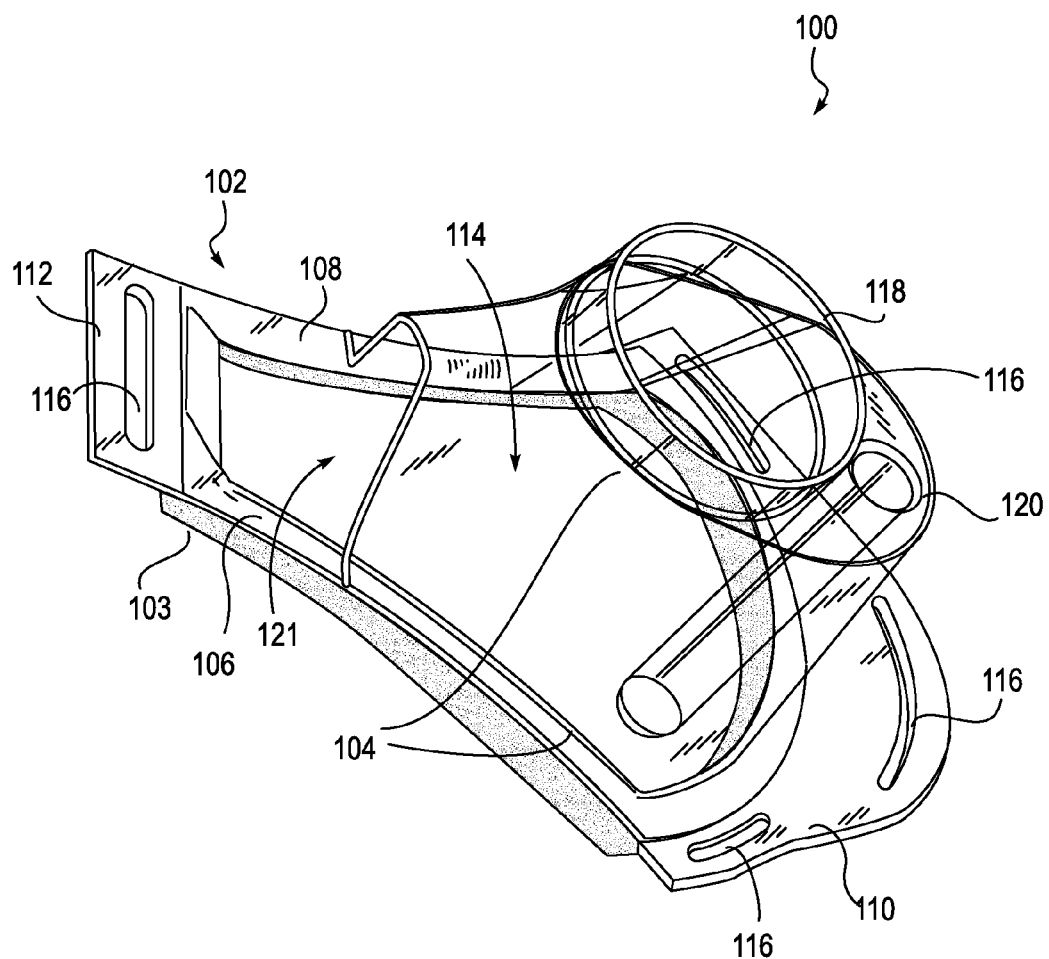
FIG. 1 illustrates one embodiment of an ultrasound coupling container.

Referring now to FIG. 1, an ultrasound coupling container 100 is shown comprising a frame 102 and a pliable reservoir portion 104. The ultrasound coupling container 100 is configured to acoustically couple an ultrasound therapy transducer to a patient to allow for movement of the ultrasound therapy transducer relative to the patient during treatment while maintaining acoustic communication between the transducer and the target tissue undergoing therapy.

Frame 102 can comprise a pliable material that is configured to conform to a patient's skin and provide a liquid seal against the patient's skin. The frame may also include, for example, foam or another conforming material 103 to improve the liquid seal between the frame to skin interface. Referring still to FIG. 1, frame 102 may comprise laterally opposed first and second frame portions 106 and 108, and longitudinally opposed third and fourth frame portions 110 and 112 to define a treatment aperture 114. Frame 102 may incorporate straps or belts (not shown) through slits 116, and/or adhesives to help secure the frame of the ultrasound coupling container to the patient's skin to form a liquid seal against the patient's skin.

As shown in FIG. 1, reservoir portion 104 can be attached to frame 102 and can extend outward from the frame and aperture 114. Reservoir portion may include transducer receptacle 118 configured to hold and position an ultrasound therapy transducer over treatment aperture 114. The reservoir portion can comprise a flexible, pliable material and is configured to allow for positioning and movement of an ultrasound therapy transducer over the treatment aperture 114 during set-up and treatment. In some embodiments, the reservoir portion 104 comprises a pliable, transparent plastic. The transparent plastic construction facilitates direct visual access to the patient and the contents of the ultrasonic medium container, which can assist the operator with set-up and monitoring throughout the treatment procedure. In the embodiment shown in FIG. 1, the reservoir portion 104 includes an opening 121, which can be used to fill the reservoir portion with an acoustic coupling medium such as degassed water, for example. Because the frame 102 defines an open aperture 114, acoustic coupling medium is allowed to be in direct contact with the patient's skin when the reservoir portion 104 is filled.

The pliable nature of the reservoir portion 104 allows the transducer receptacle 118, and thus the ultrasound transducer inserted therein, to be moved with respect to the patient and the frame. In therapeutic applications such as Histotripsy, where the relative position of the therapy transducer with respect to the target tissue must be adjusted to align a therapy focal point with the target tissue, it is necessary to be able to move the therapy transducer while maintaining acoustic communication between the transducer and the patient. Thus, in FIG. 1 when the reservoir portion is filled with an acoustic coupling medium and the reservoir portion is compressed (e.g., during positional adjustment of the therapy transducer), then acoustic coupling medium may be allowed to spill out of the opening 121 in response to the change in volume of the reservoir portion.

The reservoir portion 104 can further include a sheath 120 for acoustically coupling a rectal ultrasonic imaging probe (not shown) to the patient. The sheath can be a pliable and liquid impermeable, similar to a condom. This "condom" like sheath 120 can provide a liquid seal barrier for coupling the rectal ultrasonic imaging probe to the ultrasound coupling container and also can act as the protective barrier for inserting the rectal ultrasonic imaging probe into the patient's rectum, as it is typically done in urological trans-rectal imaging.

Figure 2:
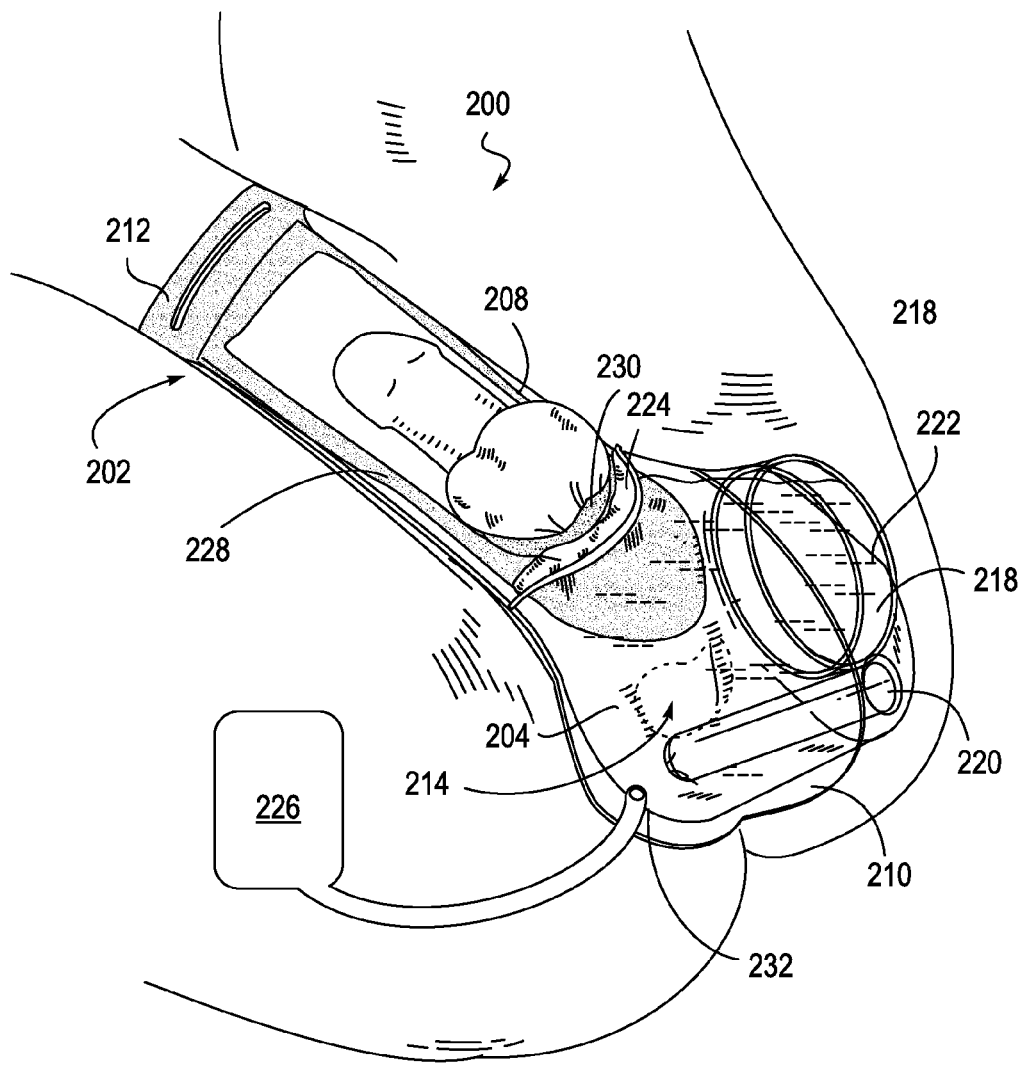
FIG. 2 illustrates one embodiment of an ultrasound coupling container attached to a patient.

Referring now to FIG. 2, an ultrasound coupling container 200 is shown positioned on a male patient. As seen in FIG. 2, frame 202 can be positioned on the patient so that first and second frame portions 206 and 208 are sized and configured to conform to each side of the patient's groin. Third frame portion 210 can be sized and configured to conform to the patient's skin below the rectum, and fourth frame portion 212 can be sized and configured to conform to the patient's skin above the penis. It can be seen that frame 202 completely surrounds the patient's penis, testicles, perineum, and rectum.

When the ultrasound coupling container 200 is positioned as shown in FIG. 2, transducer receptacle 218 can be positioned directly above the patient's perineum so as to have a direct acoustic window towards the prostate. Sheath 220 can then be aligned with the patient's rectum to allow for insertion of a rectal ultrasonic imaging probe for trans-rectal imaging of the prostate.

The pliable nature of the reservoir portion 204 allows the transducer receptacle 218, and thus the ultrasound transducer inserted therein, to be moved with respect to the patient and the frame. In the embodiment of FIG. 2, the ultrasound coupling container 200 is shown filled with an acoustic coupling medium 222 to provide acoustic communication between the transducer receptacle 218 and the patient. It can be seen that the aperture 214 defined by frame 202 allows the acoustic coupling medium 222 to directly contact the patient's skin in the region surrounding the perineum. Furthermore, in contrast to the embodiment of FIG. 1 which included an opening 121 to allow spillover of acoustic coupling medium, the embodiment of FIG. 2 can include a seal 224 to keep the acoustic coupling medium 222 fully contained within the device. When reservoir portion 204 is filled with an acoustic coupling medium the acoustic coupling medium is allowed to be in direct contact with the patient's skin. However, movement of the therapy transducer can cause the volume of the reservoir portion to change, so the ultrasound coupling container 200 of FIG. 2 can further include a remote reservoir 226 coupled to the reservoir portion. The remote reservoir can be configured to receive excess acoustic coupling medium from the reservoir portion when the reservoir portion is compressed, and can be configured to deliver additional acoustic coupling medium to the reservoir portion when the reservoir portion is expanded.

The ultrasound coupling container 200 may include ports 232 for filling, maintaining and removing the acoustic coupling medium. Filling and draining the reservoir portion may be accomplished by using a gravity feed system similar to an IV bag, as shown by remote reservoir 226. Placing the remote reservoir on an IV pole at the correct height in relationship to the ultrasound coupling container can fill the reservoir portion 204 to the desired fill level and maintain the desired fill level throughout the therapeutic procedure. When treatment is complete, lowering the remote reservoir can allow for draining the ultrasound coupling container back to the remote reservoir for disposal.

Referring still to FIG. 2, the ultrasound coupling container 200 may further include a sling 228 configured to hold and support the patient's scrotum away from the perineum. The sling can provide a larger acoustic window to the prostate through the perineum of the patient. Additionally, the sling 228 may include padding 230 around the patient's penis to increase patient comfort.

During a Histotripsy procedure, the patient can positioned in the extended lithotomy position and the ultrasound coupling container 200 can be applied to the patient's skin. With the ultrasound coupling container secured to the patient, a rectal ultrasonic imaging probe can be prepared and inserted into the sheath 220 and the patient's rectum for imaging of the prostate. Once the rectal ultrasonic imaging probe is positioned and coupled to the ultrasound coupling container, an ultrasound therapy transducer can be coupled to the transducer receptacle 218 and be initially positioned for ultrasound therapy delivery. With the patient, rectal ultrasonic imaging probe, and ultrasound therapy transducer all coupled to the ultrasound coupling container, the container can then be filled with the acoustic coupling medium.

Figure 3:
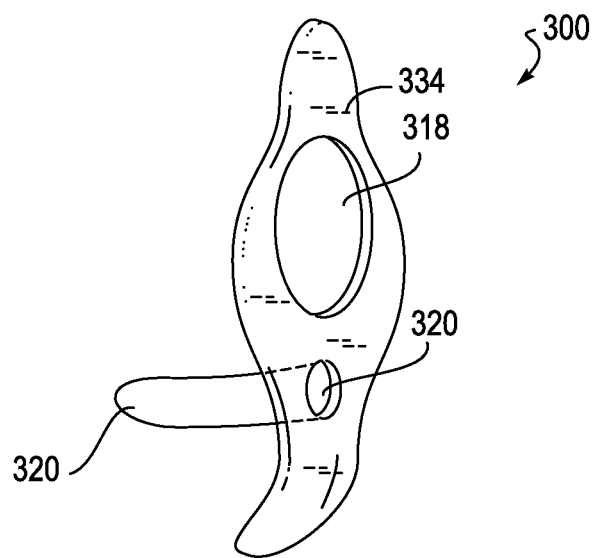
FIG. 3 illustrates another embodiment of an ultrasound coupling container.

FIG. 3 is one embodiment of an ultrasound coupling container 300, which is a variation of the coupling containers described above. In FIG. 3, the ultrasound coupling container 300 comprises a pouch 334 that can be applied directly to the patient's perineal region, such as with an adhesive, to create an acoustic seal against the patient's skin.

The pouch 334 can further include a transducer receptacle 318 configured to couple to an ultrasound therapy transducer, thus forming a pliable reservoir pouch in the perineal region that allows for movement of the ultrasound therapy transducer during treatment and set-up. Additionally, the pouch can include a sheath 320 configured to receive a rectal ultrasonic imaging probe for imaging of the prostate.

The pouch 334 can be sealed and filled with an acoustic coupling medium, such as degassed water. The pouch 334 may optionally include ports for filling, maintaining and removing the acoustic coupling medium. In some embodiments, the pouch can comprise a transparent plastic that enables the surgeon to directly view the perineum. In contrast to the ultrasound coupling containers described above in FIGS. 1-2, the pouch 334 does not allow the acoustic coupling medium to directly contact the patient's skin. Instead, the acoustic coupling medium is fully contained within the pouch to allow for shipping and transport of a fully filled pouch.

Referring still to FIG. 3, pouch 334 can be sized and shaped to cover only the perineal region of a male patient. Thus, the pouch may extend laterally between each side of the groin, and may extend longitudinally from just above the perineum to below the rectum. When placed on a patient, the sheath 320 is configured to align with the patient's rectum and the transducer receptacle 318 is configured to align with the patient's perineum.

Figure 4:
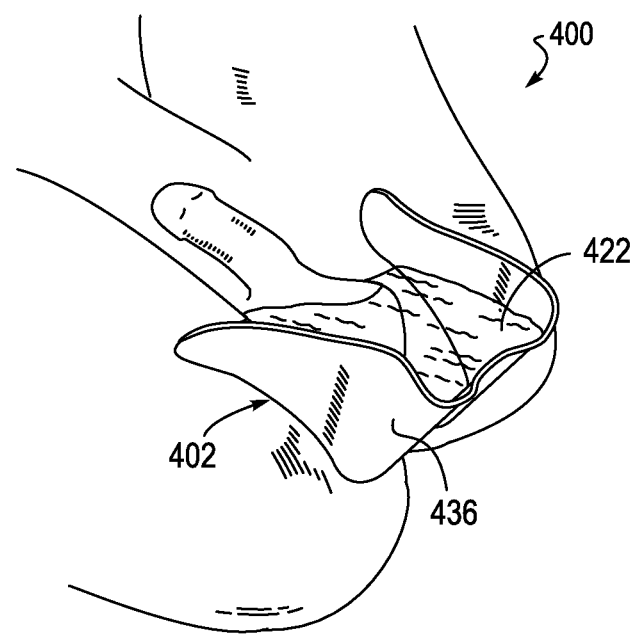
FIG. 4 illustrates one embodiment of an ultrasound coupling container attached to a patient.

FIG. 4 illustrates yet another embodiment of an ultrasound coupling container 400, comprising a plurality of walls 436 to form a "dam" like structure. The embodiment of FIG. 4 includes three walls 436, but any number of walls can be used to form a reservoir of acoustic coupling medium 422 against the patient's skin. The walls 436 include a pliable frame 402 configured to conform to a patient's skin and provide a liquid seal against the patient's skin. In the embodiment of FIG. 4, the frame can conform to the patient's skin along either side of the groin as well as below the rectum and perineum.

During therapy, an ultrasound therapy transducer can be immersed in the acoustic coupling medium 422, providing acoustic communication between the transducer and the patient. The reservoir of acoustic coupling medium can be large enough to allow for movement of the ultrasound therapy transducer during treatment. In some embodiments, the reservoir level is allowed to rise and fall against the walls 436 as the transducer is inserted and pulled from the reservoir. In other embodiments, the ultrasound coupling container 400 includes ports for filling, maintaining and removing the acoustic coupling medium.

The ultrasound coupling container may incorporate straps, belts, and/or adhesives, as described above, to help secure it to the patient and form the liquid seal against the patient's skin. The ultrasound coupling container may be formed from a transparent plastic that enables the surgeon to directly view the perineum, for example.

Figure 5:
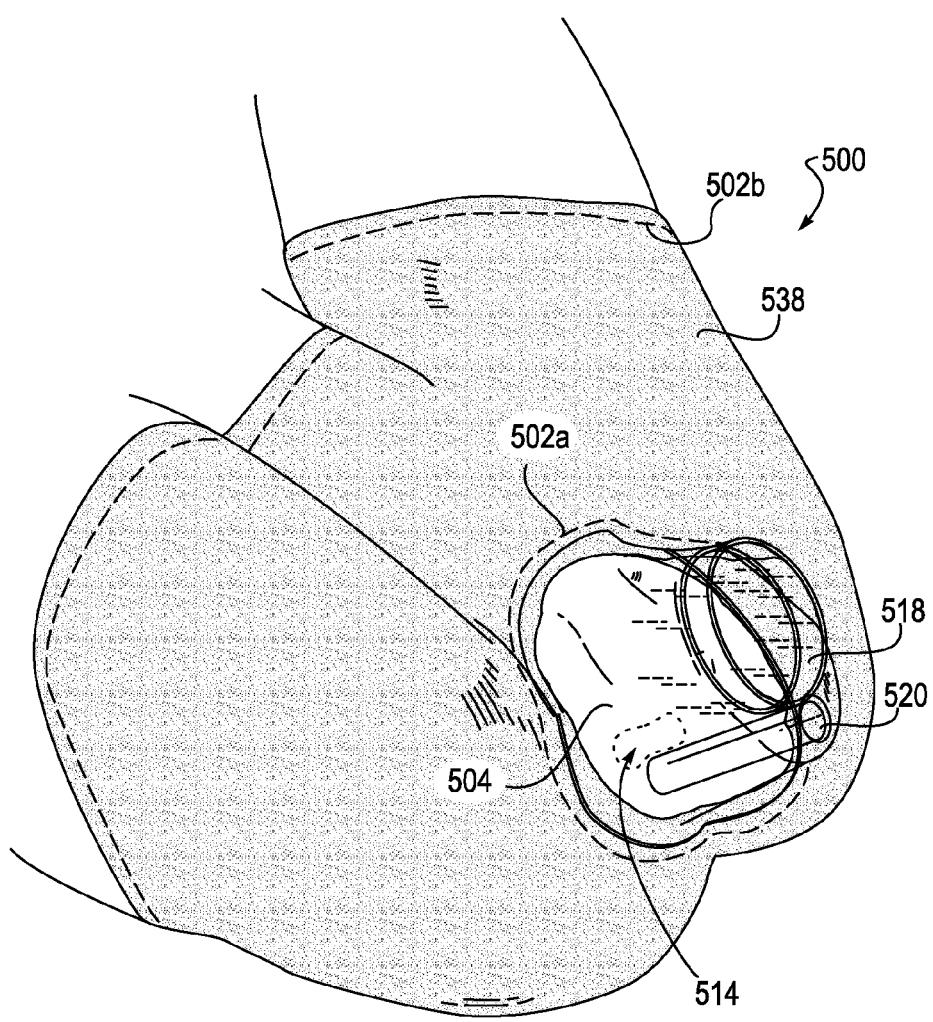
FIG. 5 illustrates one embodiment of an ultrasound coupling container in the form of a garment worn by a patient.

FIG. 5 illustrates an additional embodiment of an ultrasound coupling container 500, which is implemented as a wearable "shorts" or "boxers" type garment 538. The ultrasound coupling container 500 includes many of the same features described above with respect to ultrasound coupling container 200 of FIG. 2, including reservoir portion 504, transducer receptacle 518, and sheath 520. The garment 538 may optionally include an opening, pouch, zipper, or other mechanism in the garment to gain access to the penis, such as for catheter placement/removal as well as cystoscopy as needed.

As described above, ultrasound coupling container 500 provides a liquid seal against the patient's skin and acoustically couples an ultrasound therapy transducer to the patient. The reservoir portion 504 can be filled with an acoustic coupling medium, and can be formed from a pliable material so as to allow for movement of the ultrasound therapy transducer during treatment. In the embodiment of FIG. 5, the acoustic coupling medium is allowed to be in direct contact with the patient's skin when the reservoir portion 504 is filled. The reservoir portion may additional include ports for filling, maintaining and removing the acoustic coupling medium.

Referring still to FIG. 5, the ultrasound coupling container 500 can provide a liquid seal to the patient's skin in a variety of ways. In one embodiment, the garment 538 can include a frame 502a surrounding the reservoir portion to provide a liquid seal around the patient's perineal region and rectum. When the garment is worn by the patient, the reservoir portion can be configured to surround the perineal area, and the sheath 520 can be configured to align with the patient's rectum. The frame 502a may be attached to the patient's skin with an adhesive and/or straps, or may contain inflatable bladders to improve the liquid sealing mechanism against the patient's skin. When the frame 502a is sealed against the patient's skin, the reservoir portion may be filled with an acoustic coupling medium.

In another embodiment, frame 502b may be used to provide a liquid seal between the garment and the patient's skin. In this embodiment, frame 502b can attached to the patient's skin with an adhesive and/or straps, or may contain inflatable bladders to improve the liquid sealing mechanism against the patient's skin. When the frame 502b is sealed against the patient's skin, the entire garment including the reservoir portion may be filled with an acoustic coupling medium. However, this embodiment requires more acoustic coupling medium to be used than if only frame 502a is sealed to the skin.

Figure 6:
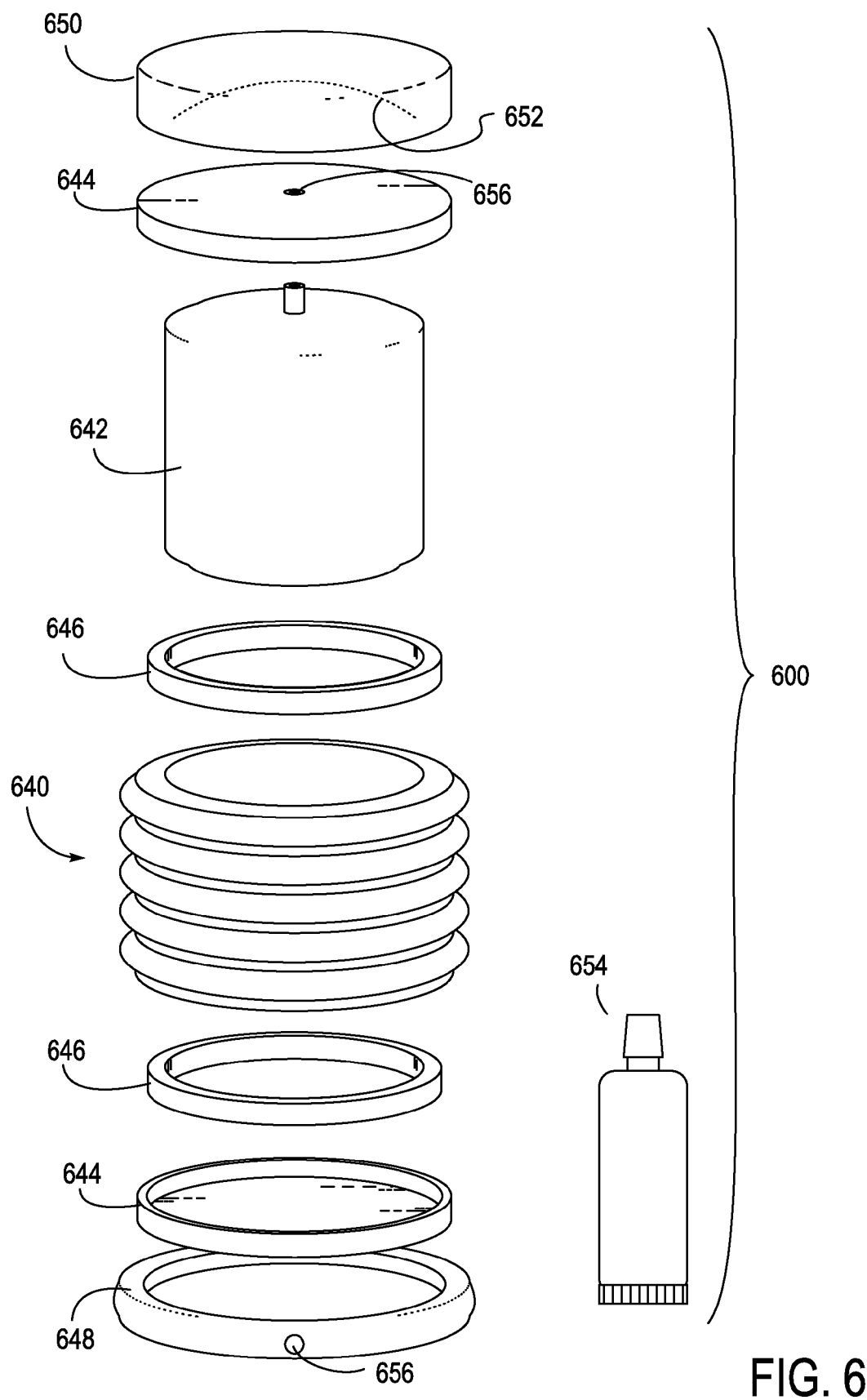
FIG. 6 is an exploded view of one embodiment of an ultrasound coupling container.

FIGS. 6-10 illustrate several embodiments of an ultrasound coupling container. FIG. 6 is an exploded view of an ultrasound coupling container 600, comprising bellows 640 containing highly compliant inner bladder 642, which can be filled with an acoustic coupling medium. The bellows 640 can be sealed at both ends with caps 644 to contain the bladder and acoustic coupling medium during storage and shipping.

The bellows can be constructed of plastic, preferably polypropylene (PP), polyvinyl chloride (PVC), silicone (SI), or polyethylene formulations which are commonly used to make bellows and components with living hinges and flexibility. Plastic bellows can be fabricated economically by blow molding (PP, PVC, and PE), injection molding (PE and SI) or dip coating (PVC). Bellows 640 can also be formed from metals such as titanium or stainless steel; however these are relatively expensive.

The bellows can be made with an extension 646 that may include integral screw threads, snap fittings, bayonet locks or other fittings for attaching to the end caps 644. Alternatively, the caps can be attached with a separate piece that connects to the bellows with an adhesive, a weld, or other attachment methods. The caps 644 can facilitate attachment of an ultrasound therapy transducer 650 having a concave surface 652 on one end of the ultrasound coupling container and a skin adapter 648 on the other end of the ultrasound coupling container at the skin interface.

The inner bladder 642 can be fabricated from highly compliant elastic materials such as silicone, polyurethane, latex, rubber or other such material. The bladder can be filled with an acoustic coupling medium, such as degassed water or a gel (phantom gel). The bladder may include vents 656 for filling or emptying the acoustic coupling medium from the bladder.

In use, the caps 644 can be removed from each end of the ultrasound coupling container to expose the inner compliant bladder 642. The ultrasound therapy transducer 650 can be attached to the top of the ultrasound coupling container, and a skin adapter 648 may be placed on the bottom of the ultrasound coupling container to provide a better seal and improved patient comfort. The skin adapter can be a highly compliant ring fabricated from a sealed foam, an air filled bladder, or other such material. The patient's skin can then be prepped with standard ultrasonic coupling gel 654, which can also be applied to the surface of the ultrasound therapy transducer 650. The ultrasonic coupling gel assures proper transmission of ultrasound at these surfaces.

Figure 7:
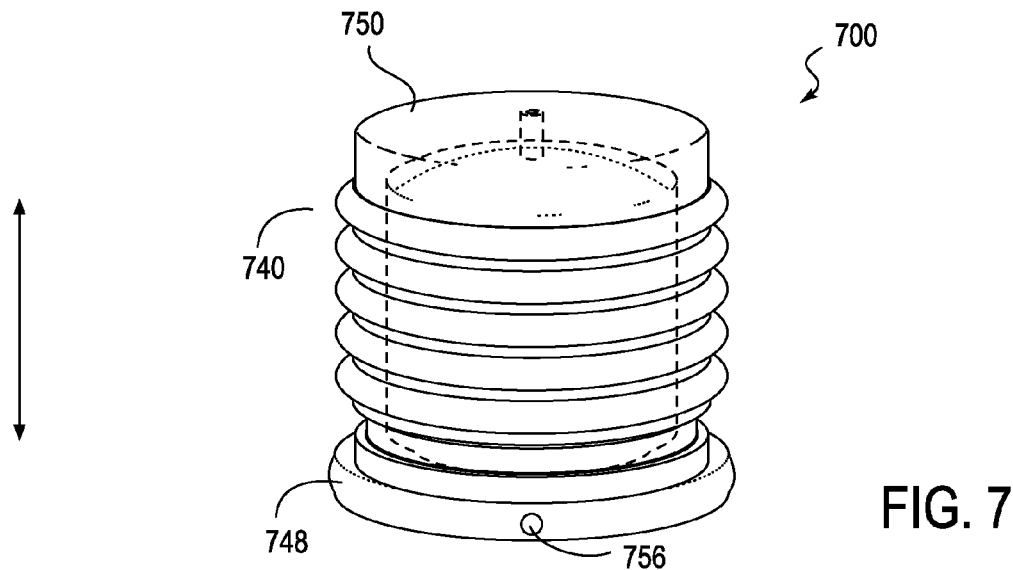
FIGS. 7-8 are additional views of the ultrasound coupling container of FIG. 5.
Figure 8:
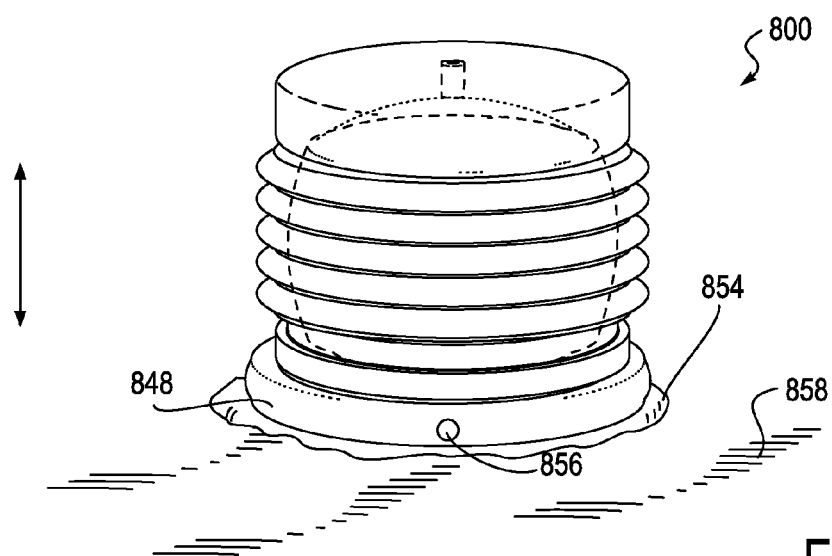

FIG. 7 illustrates the ultrasound coupling container 700 in a relaxed, expanded configuration. FIG. 8 illustrates ultrasound coupling container 800 in a compressed configuration against the patient's skin. In FIG. 8, the compliant bladder is forced down on the patient's skin and up into the ultrasound therapy transducer 850. The bladder can then conform to the concave surface 852 of the ultrasound therapy transducer and also the curves on the patient's skin surface. Vents 856 can be provided at the top or at other locations in the ultrasound therapy transducer to facilitate conformance of the bladder to the concave surface. In some embodiments, the vents can include a one way valve that allows air to escape and not return from the space between the bladder and concave surface. In this manner, the one way valve vent can create a vacuum in the space between the bladder and the concave surface. Similarly, a vent 856 in the skin adapter at the patient skin surface 858 can be provided to facilitate conformance of the bladder to the curves on the skin surface. This vent may also include a one way valve to facilitate creation of a vacuum between the bladder and patient skin surface.

Figure 9:
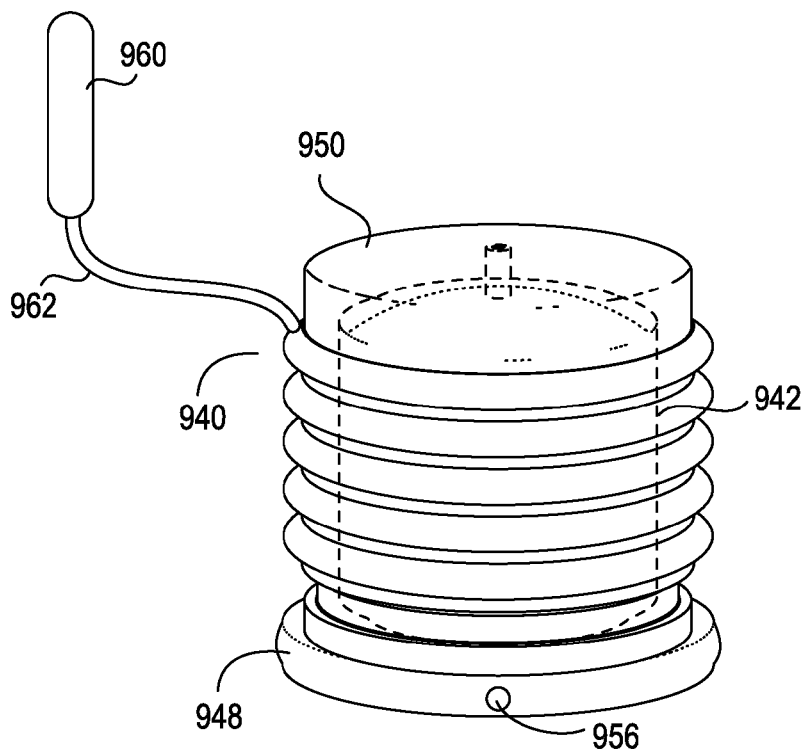
FIGS. 9-10 illustrate one embodiment of an ultrasound coupling container having a remote reservoir.
Figure 10:
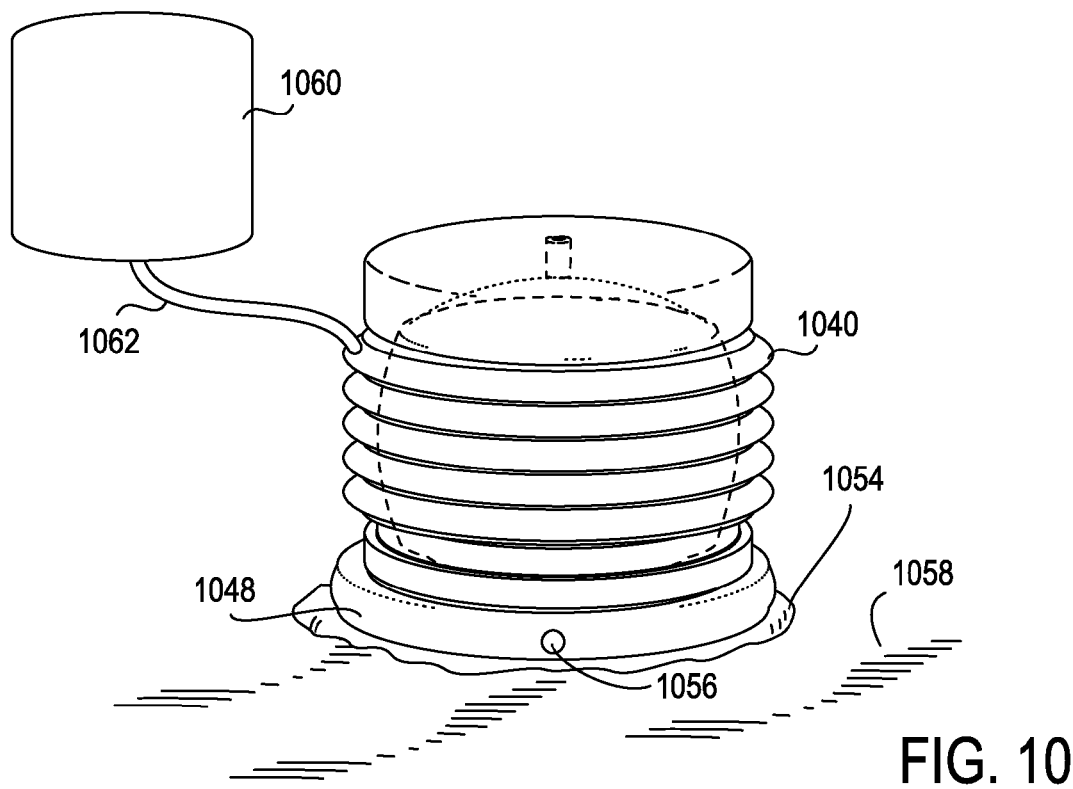

The embodiments illustrated above in FIGS. 6-8 may be enhanced with a remote reservoir that enables more compression and expansion of the ultrasound coupling container during use. Referring now to FIGS. 9-10, remote reservoir 960 is connected to the bellows 940 or bladder 942 with tubing 962. Referring now to FIG. 10, the remote reservoir bag can expand with the acoustic coupling medium when the bellows 1040 are compressed, and deliver acoustic coupling medium to the bellows or bladder when the bellows are expanded during Histotripsy treatment.

The remote reservoir can be a bag or other compliant or rigid container. A rigid container would require a vent. A remote reservoir can be similar to an intravenous solution bag that made from PVC or other suitable plastic film. The tubing can be made of PVC or other suitable flexible plastic material. In use, the remote reservoir can be elevated to increase the pressure within the remote reservoir to provide better contact with the bladder skin surfaces.

Methods of treating a prostate with the devices and systems described herein are also provided. In one embodiment, a method of treating a prostate of a patient comprises imaging the prostate with an ultrasound probe, placing an acoustic medium container over a perineum of the patient, and applying ultrasonic therapy through the acoustic medium container to cause mechanical fractionation of a target portion of the prostate.

The acoustic medium container can be any of the acoustic medium containers described herein and throughout FIGS. 1-10.

The prostate can be imaged by inserting the ultrasound probe into the patient's rectum to image the prostate. In some embodiments, the ultrasound probe is inserted into a rectal sheath to provide a liquid seal barrier between the ultrasound probe and the patient's rectum.

In some embodiments, the method comprises at least partially filling the acoustic medium container with an acoustic coupling medium, such as degassed water. In some embodiments, the acoustic coupling medium directly contacts the patient's skin. In other embodiments, the acoustic coupling medium does not directly contact the patient's skin.

In some embodiments, the method further comprises securing the acoustic medium container to the patient with an adhesive. In other embodiments, the method comprises securing the acoustic medium container to the patient with a strap. The acoustic medium container can be secured to the patient to form a liquid seal between the container and the patient's skin.

The applying step can further comprise applying ultrasonic therapy with an ultrasonic therapy transducer coupled to the acoustic medium container. In some embodiments, the applying ultrasonic therapy step comprises applying histotripsy to treat the patient. In other embodiments, the applying ultrasonic therapy step comprises forming cavitation bubbles in the target portion of the prostate. In additional embodiments, the applying ultrasonic therapy step comprises applying acoustic pulses that operate at a frequency between approximately 50 KHz and 5 MHz, having a pulse intensity with a peak negative pressure of approximately 8-25 MPa, a peak positive pressure of more than 10 MPa, a pulse length shorter than 50 cycles, a duty cycle between approximately 0.1% and 5%, and a pulse repetition frequency of less than 5 KHz. In additional embodiments, the applying ultrasonic therapy step comprises applying lithotripsy or HIFU to treat the patient.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An ultrasound therapy device, comprising:
    a frame configured to conform to and provide a liquid seal against a patient's skin, the frame defining an open aperture;
    a rectal imaging probe configured to image a patient's prostate;
    a reservoir portion configured to hold an acoustic coupling medium, the reservoir portion being configured to provide the acoustic coupling medium in direct contact with the patient's skin through the open aperture, the reservoir portion further comprising a sheath configured to receive the rectal imaging probe; and
    an ultrasound transducer coupled to the frame and in acoustic communication with the acoustic coupling medium, wherein movement of the ultrasound transducer relative to the frame maintains acoustic communication between the ultrasound transducer and the acoustic coupling medium.

2. The ultrasound therapy device of claim 1 wherein the frame is sized and shaped to conform to a male patient's anatomy surrounding the perineum.

3. The ultrasound therapy device of claim 2 further comprising a sling configured to hold the patient's scrotum away from the perineum.

4. The ultrasound therapy device of claim 1 further comprising an opening in the reservoir portion configured to expose the acoustic coupling medium to air.

5. The ultrasound therapy device of claim 1 wherein the acoustic coupling medium comprises a degassed water.

6. The ultrasound therapy device of claim 1 wherein the frame is configured to be secured to the patient with an adhesive.

7. The ultrasound therapy device of claim 1 wherein the frame is configured to be secured to the patient with a strap.

8. The ultrasound therapy device of claim 1 wherein the frame comprises a wearable garment.

9. The ultrasound therapy device of claim 8 wherein the wearable garment is configured to provide a liquid seal against the patient's skin near the patient's waist and near the patient's legs.

10. The ultrasound therapy device of claim 8 wherein the wearable garment is configured to provide a liquid seal against the patient's skin around the patient's perineum.

11. The ultrasound therapy device of claim 1 further comprising a remote reservoir configured to receive the acoustic coupling medium from the reservoir portion when the reservoir portion is compressed and to deliver the acoustic coupling medium to the reservoir portion when the reservoir portion is expanded.

12. The ultrasound therapy device of claim 1 wherein the ultrasound transducer is configured to deliver a histotripsy pulse to the patient's prostate.

13. The ultrasound therapy device of claim 1 wherein the ultrasound transducer is configured to form cavitation bubbles in the patient's prostate.

14. The ultrasound therapy device of claim 1 wherein the ultrasound transducer is configured to deliver acoustic pulses that operate at a frequency between 50 KHz and 5 MHz, having a pulse intensity with a peak negative pressure of 8-25 MPa, a peak positive pressure of more than 10 MPa, a pulse length shorter than 50 cycles, a duty cycle between 0.1% and 5%, and a pulse repetition frequency of less than 5 KHz.

15. The ultrasound therapy device of claim 1 wherein the sheath extends through the reservoir portion and provides a liquid seal barrier for inserting the rectal imaging probe into the patient's rectum.

* * * * *